(12) United States Patent
Bousman et al.

(10) Patent No.: US 6,451,772 B1
(45) Date of Patent: Sep. 17, 2002

(54) BIOPOLYMER SALTS WITH LOW ENDOTOXIN LEVELS, BIOPOLYMER COMPOSITIONS THEREOF AND METHODS OF MAKING THE SAME

(75) Inventors: William S. Bousman; George T. Colegrove, both of San Diego; Robert Raczkowski; Monica A. Garcia, both of Chula Vista, all of CA (US); John L. Holahan, III, University City, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/438,975

(22) Filed: Nov. 12, 1999

Related U.S. Application Data
(60) Provisional application No. 60/108,439, filed on Nov. 13, 1998.

(51) Int. Cl.$^7$ .............................................. A61K 31/715
(52) U.S. Cl. ........................ 514/54; 514/183; 514/345; 424/282.1
(58) Field of Search ..................... 514/54, 183, 345; 424/282.1

(56) References Cited

U.S. PATENT DOCUMENTS 5,589,591 A    12/1996    Lewis

FOREIGN PATENT DOCUMENTS

| JP | 08-269102 | * | 10/1996 |
| WO | WO 93 13136 A | | 7/1993 |
| WO | WO 95/05803 | * | 3/1995 |

OTHER PUBLICATIONS

Pryogens Endotoxins, LAL Testing, and Depyrogenation, Frederick C. Pearson, III; copyright Marcel Dekker Inc., 1986; New York, NY, pp. 204–218.

Chemical Abstracts, vol. 126, No. 5, Abstract No. 61798, "Endotoxin–free .beta.–1,3–glucans, their manufacture and medical gels containing them", XP002134037, dated Feb. 3, 1997.

PCT/US99/27067 International Search Report, date mailed Apr. 18, 2000.

* cited by examiner

Primary Examiner—Ralph Gitomer
Assistant Examiner—Devesh Khare
(74) Attorney, Agent, or Firm—Banner & Witcoff, Ltd.

(57) ABSTRACT

The present invention is directed towards biopolymer salts and biopolymer compositions comprising a biopolymer salt having an endotoxin content less than about 100 endotoxin units per gram. Because of their low endotoxin content, the biopolymer salts and biopolymer compositions of this invention may be administered parenterally to a patient. The present invention is also directed to methods of preparing the compositions of this invention.

23 Claims, No Drawings

BIOPOLYMER SALTS WITH LOW ENDOTOXIN LEVELS, BIOPOLYMER COMPOSITIONS THEREOF AND METHODS OF MAKING THE SAME

This application claims the benefit of U.S. Provisional application No. 60/108,439 filed Nov. 13, 1998.

BACKGROUND OF THE INVENTION

1. Field of the Invention

This invention relates to biopolymer salts having low levels of endotoxin and to biopolymer compositions thereof. The biopolymer salts of this invention are particularly useful as parenteral implants. The invention also relates to methods of purifying biopolymer salts, such as alginates and biogums, to prepare the novel biopolymer salts having low endotoxin content.

2. Background of the Invention

Materials which are to be used parenterally in the body must be essentially free of pyrogens, which are materials that induce fever by triggering an immune response. Introduction of pyrogenic materials into the body can produce a reaction severe enough to produce shock or even death. An important pyrogenic material is the lipopolysaccharide endotoxin which exist as a component of the cell walls of gram negative bacteria. These endotoxins are released in large quantities when the gram negative cells undergo lysis. Materials which come into contact with water having high gram negative bacterial counts can be expected to contain significant quantities of lipopolysaccharide endotoxin. Although this does not pose a problem for compositions that are administered orally, it is unacceptable for parenterally administered compositions.

Lipopolysaccharide endotoxin is not a living material and cannot be deactivated by common sterilization techniques such as autoclaving. While gamma irradiation and dry heat sterilization techniques do destroy endotoxin, these techniques also may destroy or damage many other compounds in the composition. Therefore, many sterile products can contain significant levels of endotoxin unless the endotoxin is specifically removed or deactivated.

In addition, because the lipopolysaccharide originates from gram negative bacteria, non sterile material that was originally endotoxin free can become contaminated with endotoxin as the organisms multiply. Endotoxin free products also can become contaminated after contacting surfaces containing endotoxin; these are primarily surfaces that have contacted water. Thus a composition which is to be administered parenterally must be free of endotoxin and must also be sterile to avoid regeneration of lipopolysaccharide endotoxin.

Biopolymer products such as alginic acid and its salts, gellan gum, and xanthan gum are known for use in a number of pharmaceutical applications, including for example, in sustained release pharmaceuticals that are orally ingested. However, these prior biopolymer products have had an endotoxin level that is not suitable for parenteral administration. For parenteral use, the endotoxin level of biopolymer salts should be less than about 100 endotoxin units per gram of biopolymer, and preferably less than 50 endotoxin units per gram of biopolymer salt. It would be highly desirable to provide biopolymer salts having an endotoxin content sufficiently low such that the biopolymer salts are suitable for parenteral administration.

SUMMARY OF THE INVENTION

The present invention is directed towards biopolymer salts that are suitable for parenteral use. In particular, this invention relates to biopolymer salts, such as alginates or biogums, having water-soluble polysaccharides that are biologically-produced and having an endotoxin content less than about 100 endotoxin units per gram. The invention is also directed to alginate or biogum compositions comprising the biopolymer salt of this invention and a pharmaceutically acceptable solvent.

Another embodiment of this invention relates to methods for preparing the biopolymer salts and compositions thereof that are suitable for parenteral use. In particular, one method comprises the steps of (i) contacting an aqueous solution of a biopolymer salt with a hydrophobic material to adsorb endotoxin on said material; and (ii) precipitating a biopolymer salt having an endotoxin content less than about 100 endotoxin units per gram from the solution by mixing a water miscible organic solvent with the solution. In yet another embodiment of the method of this invention, the step of precipitating may be replaced by the step of extracting endotoxin from the aqueous solution with a water immiscible organic solvent. These methods advantageously provide biopolymer salts and biopolymer compositions that have an endotoxin content of less than 100 endotoxin units per gram. These methods can be applied to a wide variety of biopolymer salts comprising water-soluble polysaccharides, including not only the alginates and biogums mentioned above, but also chitosan, chitan, carrageenan, agar, welan gum, S-657 gum, rhamsan gum, carboxymethylcellulose, and chemical substitutions of carboxymethylcellulose, among others. The novel biopolymer salts and compositions thereof are highly suitable for use as parenteral implants. They may also be used, for example, to supplement natural lubricating fluids, to coat catheters, to thicken parenteral injections, to provide tissue bulking, and for cell encapsulation techniques.

DETAILED DESCRIPTION OF THE INVENTION

Endotoxin levels typically are measured using the Limulus Amoebocyte Lysate (LAL) test method. There are several variations of this test method in common use (e.g., Gel-Clot Endpoint, Chromogenic LAL, Kinetic-Chromogenic LAL) which produce a visual or color response in proportion to the amount of endotoxin present. Endotoxin levels are measured in endotoxin units (eu).

The biopolymer salts and biopolymer compositions of the present invention have endotoxin levels of less than about 100 eu per gram of biopolymer salt on a dry basis. Preferably, the biopolymer salts and biopolymer compositions of the present invention have endotoxin levels less than about 50 eu per gram, and more preferably, less than about 20 eu per gram.

The biopolymer salts of this invention are water-soluble polysaccharides that are either exuded by, or are extracted from, living organisms. Alginates are salts of alginic acid, which is a copolymer composed of D-mannuronic acid and L-guluronic acid units. These units typically exist as blocks of polymannuronic acid, blocks of polyguluronic acid or blocks of alternating mannuronic and guluronic acid units. The arrangement and relative amounts of mannuronic and guluronic acid are determined primarily by the source from which the alginate is manufactured. For example, most commercial alginate salts are produced by extraction from brown seaweeds. Alginate produced from *Macrocystis pyrifera* has a mannuronic to guluronic unit ratio (M/G ratio) of about 1.56:1 while alginate produced from *Laminaria hyperborea* has an M/G ratio of about 0.45. Monovalent salts (sodium or potassium salts) of alginate are typically water soluble while divalent salts (calcium, barium), polyvalent salts (iron, aluminum, etc.) and alginic acid form water insoluble gels or solids. Alginates are commercially available from ISP Alginates (San Diego, Calif.).

Biogums are salts of complex organic acids and are produced by fermentation of microrganisms. Gellan gum refers to the extracellular polysaccharide obtained from microorganisms of the species *Sphingomonas elodea*, in a suitable nutrient medium. Similarly, xanthan gum is a hydrophilic polysaccharide which is obtained by fermentation of microorganisms of the genus Xanthomonas, in a suitable nutrient medium. Gellan gum and xanthan gum are useful viscosifying agents. Gellan gum is also useful as a gelling agent. Depending on the biogum, monovalent salts (sodium or potassium salts) typically, but not necessarily, will render the biogum water soluble while divalent salts (magnesium, calcium, barium) and polyvalent salts (iron, aluminum, etc.) in the biogum may, but not necessarily, form water insoluble gels or solids.

The biopolymer employed in this invention is an alginate or biogum. The alginate is a salt of alginic acid, whereas the biogum is a salt of a complex organic acid, typically with a long polymer chain that increases viscosity.

Most preferably, with regards to alginates, the salt is sodium alginate. The alginate will typically have a ratio of mannuronic acid to guluronic acid of about 0.3:1 to about 2:1. In general, high mannuronic acid alginates have a ratio greater than 1 while high guluronic acid alginates have a ratio less than 1.

An example of a preferred source of alginate which maybe used in preparing the purified alginates of the present invention is "KELTONE", which is available from ISP Alginates (San Diego, Calif.). KELTONE LVCR is obtained from *Macrocystis pyrifera* giant kelp, and is a high mannuronic acid content alginate, having a ratio of mannuronic acid to guluronic acid of about 1.56:1.

Typically, commercially available KELTONE LVCR has an endotoxin level in the range from about 30,000 eu per gram to about 60,000 eu per gram. Pharmaceutical compositions for parenteral administration typically should have no more than about 100 eu per gram. Consequently, before KELTONE LVCR may be used in used in a parenteral application, the level of endotoxin must be reduced substantially. This invention provides a method for reducing the level of endotoxin in known salts of alginic acid, such as KELTONE LVCR, to below about 100 eu per gram.

Two examples of a preferred source of biogum which may be used in preparing the purified biogum of the present invention are "GELRITE" gellan gum, derived from the microoganism *Sphingomonas elodea*, or "KELTROL T" xanthan gum, which is derived from the microorganism *Xanthanomas campestris*. Both biogums are available from Kelco Biopolymers (San Diego, Calif.). Typically, commercially available GELRITE gellan gums or KELTROL T xanthan gums are produced from gram negative bacteria and consequently are found to have endotoxin levels over 1,000,000 eu per gram. Removing these exceedingly high loads of endotoxin from the biopolymer in a commercially efficient manner can be particularly challenging. As described above in regards to alginates, pharmaceutical compositions for parenteral administration typically should have no more than 100 eu per gram. Consequently, before biogums may be used in a parenteral application, the level of endotoxin must be dramatically reduced. This invention provides a method for reducing the level of endotoxin in known biogums to below 100 eu per gram.

The lipopolysaccharide endotoxin molecular structure consists of a lipid head and a polysaccharide tail. Without being bound by theory, it is believed that the lipid portion of the polymer induces the pyrogenic response and that removing or disrupting the lipid portion may eliminate the induced response. Since the polysaccharide tail of the endotoxin is similar in molecular structure to the biopolymer, separation of the endotoxin from the biopolymer salt is not a simple matter.

A number of techniques, which are disclosed in the literature, are employed in the pharmaceutical industry to remove endotoxin from materials. However, many of these methods would also destroy or otherwise interact unfavorably with the biopolymer molecule, making such techniques inappropriate for depyrogenation of biopolymer compositions.

The present method of this invention uses the combination of two techniques to obtain the heretofore unavailable purified biopolymer salts. In particular, it has been discovered that when these techniques are used in combination, the level of endotoxin in alginates and biogums can be reduced to less than about 100 eu per gram.

This method for preparing a biopolymer composition comprising a salt of a biopolymer having an endotoxin content less than about 100 endotoxin units per gram comprises the steps of (i) contacting an aqueous solution of a biopolymer salt with a hydrophobic material to adsorb endotoxin on said material; and (ii) precipitating the biopolymer salt having an endotoxin content less than about 100 endotoxin units per gram from the solution by mixing a water miscible organic solvent with the solution.

Generally, the starting aqueous solution will have an alginate or biogum concentration of about 0.5 to about 5 percent by weight of the solution. Most preferably, the aqueous solution is a mixture of alginate and water, or biogum and water.

As noted above, one element of the method of this invention includes the adsorption of the endotoxin onto hydrophobic materials. Without wishing to be bound by theory, it is believed that the lipid end of the endotoxin molecule is attracted to the hydrophobic material. Biopolymer salts, which are polysaccharide polymers, lack this hydrophobic character. Therefore, they are not believed to adhere to the hydrophobic material.

Preferred hydrophobic materials for use in this invention include, for example, polystyrene, polypropylene, fluorocarbon polymers such as Dupont's "TEFLON" and the like. Polypropylene and polystyrene are most preferred.

If the hydrophobic surface is used in the form of a filtration membrane, it may also be possible to physically filter cells or cell fragments from the solution, thereby further reducing the amount of endotoxin. Filtration membranes also advantageously provide an extremely large surface area for adsorption of endotoxin onto the hydrophobic surface.

If a hydrophobic filtration membrane is employed, then preferably the membrane will have a pore size of about 1.0 microns to about 0.1 microns. A particularly preferred hydrophobic filtration membrane is a polypropylene membrane having a pore size of about 0.2 microns.

Alternatively, the hydrophobic surface can be in the form of hydrophobic resins. Hydrophobic resins can provide efficient contact with high volumes of endotoxins. Hydrophobic resins provide additional advantages over filter membranes in that the hydrophobic resins can be regenerated and reused and can be easily increased in quantity to contact greater volumes of biopolymers. Hydrophobic resins are also more suitable for materials such as biogums, which are difficult to filter through the hydrophobic filter membranes due to viscosity and/or the length of the polymer chains.

As with the hydrophobic filter membranes, the hydrophobic resins can be varied in size to provide contact with a greater surface area. A particularly preferred hydrophobic resin bead of this invention is less than 0.5 mm in diameter and is comprised of polystyrene divinyl benzene.

If the hydrophobic resin method of purification is employed, a preliminary step may be required before contacting the biopolymer salt with the hydrophobic resin. The pH of the solution should first be raised to increase lipopolysaccharide endotoxin solubility before contact with the hydrophobic resin is made. Preferably, the pH is raised to at least 9 by addition of NaOH, KOH or other bases known to those skilled in the art. After contacting, the hydrophobic resin beads are sieved from the solution, and the pH is preferably adjusted back to neutral for the second purification technique of the method, as described below.

While the endotoxin lipopolysaccharide is known to bind to hydrophobic materials such as activated charcoal, polypropylene, and polystyrene, experiments using this contacting technique alone did not successfully produce a biopolymer salt having an endotoxin content of less than 100 eu per gram.

It has been discovered, however, that a highly purified biopolymer salt can be obtained by mixing the aqueous solution that was contacted with the hydrophobic surface with a water miscible organic solvent. This second step results in the precipitation of the highly purified biopolymer salt from the solution.

Without being bound to theory, it is believed that the lipid portion of the endotoxin molecule provides the molecule with solubility in hydrophobic liquids, such as hexane or methyl tert-butyl ether, or in partially hydrophobic liquids such as alcohols. In contrast, biopolymer salts will precipitate in water miscible hydrophobic liquids such alcohols and ketones which have suitably low dielectric constants. Thus, the endotoxin in the aqueous solution is separated from the biopolymer salt.

The water miscible organic precipitation solvent is selected from the group consisting of alcohols, ketones, aldehydes and mixtures thereof. Preferably, it is a low molecular weight alcohol. More preferably it is isopropyl alcohol, methanol, ethanol or acetone.

The water miscible organic solvent is typically mixed with the hydrophobic material treated aqueous solution at a volume ratio of about 1:1 to about 6:1. The mixture is held at a temperature and for a time sufficient to allow for the precipitation of the purified biopolymer salt.

After precipitation, the biopolymer salt may be dried to remove the solvent. A preferred technique of drying is low temperature oven drying (40–80° C.). Other suitable drying techniques include, but are not limited to, lyophilization and spray drying. The biopolymer salt can also be reconstituted in an acceptable solvent. A particularly preferred solvent is water.

In another embodiment of this invention, the method may be carried out by replacing the precipitation step with a liquid-liquid extraction using a water immiscible solvent. An exemplary water immiscible solvent includes hexane or methyl tert-butyl ether.

The method of this invention may include additional steps as desired. For example, in regards to alginates, it is preferable to treat the starting aqueous solution with an oxidation agent, such as 100 ppm NaOCl, to destroy the polyphenols and thereby remove color from the alginate. Alternatively, activated carbon can be contacted with the aqueous solution in lieu of the NaOCl. Most preferably, the activated carbon is added after the NaOCl to adsorb polyphenols and remove any residual NaOCl, which can breakdown alginates in storage. In addition, the step of contacting with a hydrophobic material and/or precipitation may be conducted multiple times if desired. If a filtration membrane is used it may be preferable to pass the aqueous solution through membranes having different pore sizes. For example, it may be preferred to employ a 10 micron hydrophobic membrane followed by a 0.2 micron membrane. Using this sequence will tend to improve the capacity of the smaller pore sized filter. Similarly, if hydrophobic resins are employed, the size and quantity of the hydrophobic resin beads can be varied, or layered, to maximize the available surface area available and obtain the desired level of contact.

The method of this invention is particularly advantageous because the purified biopolymer salt may be prepared using a commercial scale manufacturing process.

The biopolymer salts of this invention may be used to prepare biopolymer compositions that are suitable for parenteral administration to a patient. This may be accomplished by dissolving a biopolymer salt of this invention having an endotoxin level less than or equal to about 100 eu per gram in a pharmaceutically acceptable solvent. Preferably, the pharmaceutically acceptable solvent is water for injection. Water for injection is a certified sterile, endotoxin free and particulate free pharmaceutical grade of deionized water.

The concentration of biopolymer salt in the composition may vary between about 0.5 weight percent and about 5 weight percent, based upon the total weight of the solution. Preferably, the concentration of biopolymer salt is between about 2 weight percent and about 4 weight percent.

Many of the biopolymer compositions of this invention also include gels prepared by adding a gelling agent to the above-described biopolymer composition. These gels are suitable for parenteral administration. The gels may be made into any desired shape. For example, the gels may be made in the form of beads, sheets or filaments which may be administered to a patient. Preferred gelling agents include divalent or trivalent cations. It also may be possible to incorporate a pharmaceutically active component into the biopolymer gel before administering it to a patient.

The amount of gelling agent that may be added to the biopolymer solution to form a suitable gel may vary depending upon the concentration of biopolymer in the solution as well as upon the particular gelling agent employed. Preferably, the gelling agent is added as an aqueous solution in which the gelling agent is present at a concentration range from about 0.5% to about 10%.

The examples which follow are intended to illustrate certain preferred embodiments of the invention, an no limitation of the invention is implied.

EXAMPLE 1

Preparation of an Alginate Suitable for Parenteral Use

Three liters of a 3 percent by weight alginate solution were prepared using Keltone LVCR and water for injection. The endotoxin level of this alginate was about 61,500 eu per gram of dry alginate. All equipment which was to contact the alginate solution was depyrogenated either by heating at 250° C. for at least one hour, or by treatment with 0.1M NaOH for at least one hour. The alginate solution was treated with 200 ppm NaOCl which destroys polyphenolic colored compounds and therefore produces a colorless alginate solution.

One liter of the colorless alginate solution was then passed successively through three separate filters: a 10 μm pore size polypropylene filter, a 3 μm pore size activated carbon impregnated filter, and a 0.2 μm pore size polypropylene filter. All of the filter cartridges were manufactured by Meissner, Camarillo, Calif.

The polypropylene filter cartridges were first activated by soaking them in reagent grade isopropanol for 15 minutes prior to installing them in the filter cartridge housings and flushing them with water for injection. The activated carbon impregnated filter cartridge was flushed with water for injection to wet it and to remove carbon dust prior to use.

After the alginate solution was passed through the filter cartridges, the alginate in the filtrate was precipitated with isopropyl alcohol. Precipitation was accomplished by mixing one volume of the alginate solution with two volumes of isopropyl alcohol for 5 seconds at high speed in an Oster blender jar. The isopropanol used for precipitation was reagent grade and was obtained from a previously unopened container to avoid endotoxin contamination.

The precipitated alginate fibers were poured onto a depyrogenated 40 mesh stainless steel screen. The alginate fibers were squeezed against the screen with depyrogenated aluminum foil to remove excess solvent from the alginate. The resultant alginate fibers were then dried in an oven at 60° C. for 1–4 hours to remove the remaining solvent. The dried fibers were milled and then tested for endotoxin levels. The results of these measurements are set forth in Table 1.

EXAMPLE 2

Preparation of an Alginate Suitable for Parenteral Use

A second liter of the colorless alginate solution of Example 1 was filtered and precipitated as described in Example 1. The filters used in this Example were the same ones previously used in Example 1. After filtration, adsorption, drying and milling as in Example 1, the alginate fibers were tested for endotoxin levels. The results of these measurements are set forth in Table 1.

EXAMPLE 3

Preparation of an Alginate Suitable for Parenteral Use

A third liter of the colorless alginate solution of Example 1 was filtered and precipitated as described in Example 1. The filters used in this Example were the same ones previously used in Examples 1 and 2. After filtration, precipitation, drying and milling as in Example 1, the alginate fibers were tested for endotoxin levels. The results of these measurements are set forth in Table 1.

TABLE 1

Endotoxin Levels in Alginates

| EXAMPLE | ENDOTOXIN LEVELS (eu/g) |
| --- | --- |
| 1 | <30 |
| 2 | <30 |
| 3 | 30–60 |

As Table 1 shows, alginates which are suitable for parenteral use may be prepared from alginates having high endotoxin levels by adsorption and precipitation techniques. It is believed that the somewhat higher, but still pharmaceutically acceptable, levels of endotoxin in Example 3 are due to the limits of endotoxin adsorption of one or more the filters used in these examples. This is supported by the endotoxin levels found in the alginates prepared in the following examples, where only 2 liters of alginate solution were passed through the same filters.

EXAMPLE 4

Preparation of an Alginate Suitable for Parenteral Use

A two liter sample of the 3 percent by weight alginate solution prepared in Example 1 was treated as described in Example 1, except that this two liter sample was filtered through two 3 μm activated carbon filters rather than only one before filtering it through the 0.2 μm polypropylene filter. After filtration through previously unused filters, precipitation, drying and milling as in Example 1, the alginate fibers were tested for endotoxin levels. The results of these measurements are set forth in Table 2.

EXAMPLE 5

Preparation of an Alginate Suitable for Parenteral Use

A second two liter sample of the 3 percent by weight alginate solution prepared in Example 1 was treated as described in Example 4. After filtration through previously unused filters, precipitation, drying and milling as in Example 1, the alginate fibers were tested for endotoxin levels. The results of these measurements are set forth in Table 2.

EXAMPLE 6

Preparation of an Alginate Suitable for Parenteral Use

A fourth two liter sample of the 3 percent by weight alginate solution prepared in Example 1 was treated as described in Example 4. After filtration through previously unused filters, precipitation, drying and milling as in Example 1, the alginate fibers were tested for endotoxin levels. The results of these measurements are set forth in Table 2.

EXAMPLE 7

Preparation of an Alginate Suitable for Parenteral Use

A fourth two liter sample of the 3 percent by weight alginate solution prepared in Example 1 was treated as described in Example 4. After filtration through previously unused filters, precipitation, drying and milling as in Example 1, the alginate fibers were tested for endotoxin levels. The results of these measurements are set forth in Table 2.

TABLE 2

Endotoxin Levels in Alginates

| EXAMPLE | ENDOTOXIN LEVEL (eu/g) |
|---|---|
| 4 | 2.4 |
| 5 | <1.0 |
| 6 | 2.1 |
| 7 | <2.0 |

As Table 2 shows, the methods of this invention may be used to prepare alginates with extremely low levels of endotoxin. This may be accomplished by avoiding overloading the filters with endotoxin. Table 2 shows that when previously unused filters are used in the filtration process, the level of endotoxin in the alginate may be reduced to less than 5 eu per gram.

EXAMPLE 8

Preparation of an Alginate Suitable for Parenteral Use

Three liters of a 3 percent by weight alginate solution were prepared using Keltone LVCR and water for injection. The endotoxin level of this alginate was about 46,400 eu per gram of dry alginate.

All equipment which was to contact the alginate solution was depyrogenated either by heating at 250° C. for at least one hour, or by treatment with 0.1M NaOH for at least one hour. The alginate solution was treated with 100 ppm NaOCl which destroys polyphenolic colored compounds and therefore produces a colorless alginate solution.

The solution was then passed successively through three separate filters: two 3 μm pore size activated carbon filters in series and a 0.2 μm pore size polypropylene filter.

After the alginate solution was passed through the filter cartridges, a 300 ml portion of the alginate solution in the filtrate was mixed with the water immiscible solvent, methyl tert-butyl ether (MTBE). Extraction was accomplished by mixing one volume of the alginate solution with two volumes of MTBE at high speed in an Oster blender jar. When mixing was stopped, two layers were formed: an aqueous alginate layer on the bottom and an MTBE layer on the top. The two layers were then carefully separated. The MTBE used for extraction was reagent grade and was obtained from a previously unopened container to avoid endotoxin contamination. The extracted alginate layer was then tested for endotoxin levels. The results of these measurements are set forth in Table 3.

EXAMPLE 9

Preparation of an Alginate Suitable for Parenteral Use

A second 300 ml portion of the 3 percent by weight alginate solution that was prepared, treated, and filtered in Example 8, was precipitated with methanol. Precipitation was accomplished by mixing one volume of the alginate solution with two volumes of methanol for 30 seconds at high speed in an Oster blender jar. The methanol used for precipitation was reagent grade and was obtained from a previously unopened container to avoid endotoxin contamination.

The precipitated alginate fibers were poured onto a depyrogenated 40 mesh stainless steel screen. The alginate fibers were squeezed against the screen with depyrogenated aluminum foil to remove excess solvent from the alginate. The resultant alginate fibers were then dried in an oven at 60° C. for 1–4 hours to remove the remaining solvent. The dried fibers were milled and then tested for endotoxin levels. The results of these measurements are set forth in Table 3.

EXAMPLE 10

Preparation of an Alginate Suitable for Parenteral Use

A third 300 ml portion of the 3 percent by weight alginate solution that was prepared, treated, and filtered in Example 8, was precipitated as per the method described in Example 9, but with ethanol in lieu of methanol. The results of these measurements are set forth in Table 3.

EXAMPLE 11

Preparation of an Alginate Suitable for Parenteral Use

A fourth 300 ml portion of the 3 percent by weight alginate solution that was prepared, treated, and filtered in Example 8, was precipitated as per the method described in Example 9, but with isopropanol in lieu of methanol. The results of these measurements are set forth in Table 3.

EXAMPLE 12

Preparation of an Alginate Suitable for Parenteral Use

A fifth 300 ml portion of the 3 percent by weight alginate solution that was prepared, treated, and filtered in Example 8, was precipitated as per the method described in Example 9, but with acetone in lieu of methanol. The results of these measurements are set forth in Table 3.

TABLE 3

Endotoxin Levels in Alginates

| EXAMPLE | ENDOTOXIN LEVEL (eu/g) |
|---|---|
| 8 | <88 |
| 9 | <25 |
| 10 | <25 |
| 11 | <25 |
| 12 | <25 |

As Table 3 shows, alginates which are suitable for parenteral use may be prepared with the above-described method, using either water-miscible or water immiscible solvents.

EXAMPLE 13

Preparation of a Gellan Gum Suitable for Parenteral Use

A solution of 20 g of GELRITE gellan gum and 0.5 g sodium citrate, which sequesters polyvalent cations and improves flowability, were dissolved in 986 g of water for injection. The endotoxin level of this gellan gum solution was greater than 1,000,000 eu per gram of dry unpurified gellan gum.

All equipment which was to contact the gum solution was depyrogenated by heating at 250 μ C. for at least one hour, or by treatment with 0.1M NaOH for at least one hour. In particular, the resin beads had been previously cleaned of endotoxin and activated by soaking overnight in a 0.1 NaOH solution, rinsing with water for injection, soaking in isopropanol for 15 minutes and again rinsing with water for injection.

To this solution, 4 g of NaOH was added to raise the pH to at least 9 and increase solubility of the endotoxin. 100 g of HP-20 Polystyrene Divinyl Benzene resin beads were then added to the gellan solution and mixed overnight. All of the resin beads were manufactured by Supelco-Diainon.

The resin beads were then sieved from the solution with a screen. The pH of the solution was then adjusted back to 7 using 0.1 M HCl. The GELRITE gellan gum was then precipitated from the solution by addition of 2 volumes of isopropanol followed by mixing in an Oster blender at high speed. The precipitated fibers were sieved from the solution, dried at 50° C. overnight, and then tested for endotoxin levels. The results of these measurements are set forth in Table 4.

EXAMPLE 14

Preparation of a Xanthan Gum Suitable for Parenteral Use

A solution of 14 g of KELTROL T Xanthan gum was dissolved in 2 liters of water for injection. The endotoxin level of this xanthan gum solution was greater than 1,000,000 eu per gram of dry unpurified xanthan gum.

All equipment which was to contact the gum solution was depyrogenated by heating at 250° C. for at least one hour, or by treatment with 0.1 M NaOH for at least one hour. In particular, the resin beads had been previously cleaned of endotoxin and activated by soaking overnight in a 0.1 NaOH solution, rinsing with water for injection, soaking in methanol for 1 hour and again rinsing with water for injection.

To this solution, 8 g of NaOH was added to raise the pH to at least 9 and increase solubility of the endotoxin. 384 g of HP-20 Polystyrene Divinyl Benzene resin beads were then added to the xanthan solution and mixed overnight.

The resin beads were sieved from the solution with a screen, and the pH of the solution was then adjusted back to 7. The KELTROL T xanthan gum was then precipitated from the solution by addition of 2 volumes of isopropanol followed by mixing in an Oster blender at high speed. The precipitated fibers were sieved from the solution, dried at 60° C. for 1–4 hours, and then tested for endotoxin levels. The results of these measurements are set forth in Table 4.

TABLE 4

Endotoxin Levels in Biogums

| EXAMPLE | ENDOTOXIN LEVEL (eu/g) |
| --- | --- |
| 13 | <35 |
| 14 | 0 (NONE DETECTED) |

As Table 4 shows, the methods of this invention may be used to remove high-loaded concentrations of endotoxins from biogums. This may be accomplished by adsorption through contact with hydrophobic resins and by precipitation techniques with various solvents.

Other variations and modifications of this invention will be obvious to those skilled in the art. This invention is not limited except as set forth in the art.

What is claimed is:

1. A biopolymer salt suitable for parenteral use comprising a biopolymer salt having an endotoxin content less than about 100 endotoxin units per gram.

2. The biopolymer salt according to claim 1, wherein said endotoxin content is less than about 50 endotoxin units per gram.

3. The biopolymer salt according to claim 1, wherein said biopolymer salt is an alginate.

4. The biopolymer salt according to claim 3, wherein said biopolymer salt is sodium alginate.

5. The biopolymer salt according to claim 3, wherein said alginate is a product of *Macrocystis pyrifera* giant kelp.

6. The biopolymer salt according to claim 3, wherein said alginate is a product of *Laminaria hyperborea* kelp.

7. The biopolymer salt according to claim 1, wherein said biopolymer salt is gellan gum.

8. The biopolymer salt according to claim 7, where said gellan gum is derived from *Sphingomonas elodea*.

9. The biopolymer salt according to claim 1, wherein said biopolymer salt is xanthan gum.

10. The biopolymer salt according to claim 9, wherein said xanthan gum is derived from *Xanthamonas campestris*.

11. A biopolymer composition suitable for parenteral use comprising a biopolymer salt having an endotoxin content less than about 100 endotoxin units per gram and a pharmaceutically acceptable solvent.

12. The biopolymer composition according to claim 11, wherein said biopolymer salt is an alginate.

13. The biopolymer composition according to claim 12, wherein said alginate is sodium alginate.

14. The biopolymer composition according to claim 11, wherein said biopolymer salt is a biogum.

15. The biopolymer composition according to claim 14, wherein said biogum is gellan gum.

16. The biopolymer composition according to claim 14, wherein said biogum is xanthan gum.

17. The biopolymer composition according to claim 11, wherein said endotoxin content is less than about 50 endotoxin units per gram.

18. The biopolymer composition according to claim 17, wherein said biopolymer salt is present in an amount from about 0.5 percent to about 5 percent by weight of the composition.

19. The biopolymer composition according to claim 18, wherein said pharmaceutically acceptable solvent is water.

20. The biopolymer composition according to claim 11, further compromising a gelling agent in amount effective to form a gel of said polymer.

21. The biopolymer composition according to claim 20, wherein said gel is in the form of beads, sheets or filaments.

22. The biopolymer composition according to claim 20 wherein said gelling agent is selected from the group consisting of divalent or polyvalent cations.

23. The biopolymer composition according to claim 22 wherein said gelling agent are calcium cations.

* * * * *